(12) United States Patent
Tamizhmani et al.

(10) Patent No.: US 10,720,882 B2
(45) Date of Patent: Jul. 21, 2020

(54) SOLAR PHOTOVOLTAIC WATERLESS SOILING MONITORING SYSTEMS AND METHODS

(71) Applicants: Govindasamy Tamizhmani, Gilbert, AZ (US); Sai Tatapudi, Chandler, AZ (US)

(72) Inventors: Govindasamy Tamizhmani, Gilbert, AZ (US); Sai Tatapudi, Chandler, AZ (US)

(73) Assignee: Arizona Board of Regents on behalf of Arizona State University, Scottsdale, AZ (US)

(*) Notice: Subject to any disclaimer, the term of this patent is extended or adjusted under 35 U.S.C. 154(b) by 253 days.

(21) Appl. No.: 15/983,375

(22) Filed: May 18, 2018

(65) Prior Publication Data
US 2018/0337633 A1 Nov. 22, 2018

Related U.S. Application Data

(60) Provisional application No. 62/507,968, filed on May 18, 2017.

(51) Int. Cl.
*G01N 27/00* (2006.01)
*H02S 50/10* (2014.01)
(Continued)

(52) U.S. Cl.
CPC ............ *H02S 50/10* (2014.12); *G01N 27/414* (2013.01); *G01N 27/4145* (2013.01);
(Continued)

(58) Field of Classification Search
CPC ......... H01L 2924/0002; H01L 2924/00; H01L 22/34; H01L 2924/00014; G01N 27/4148;
(Continued)

(56) References Cited

U.S. PATENT DOCUMENTS

| | | | |
|---|---|---|---|
| 2009/0166494 A1* | 7/2009 | Bartelt-Muszynski | H02S 20/23 248/237 |
| 2011/0214368 A1* | 9/2011 | Haddock | F24S 25/615 52/173.3 |

(Continued)

FOREIGN PATENT DOCUMENTS

| | | |
|---|---|---|
| WO | 2006057704 A2 | 6/2006 |
| WO | 2015191699 A1 | 12/2015 |
| WO | 2014122705 A1 | 8/2018 |

OTHER PUBLICATIONS

J. Cano, "Photovoltaic Modules: Effect of Tilt Angle on Soiling," MS Thesis, Arizona State University, 2011.
(Continued)

*Primary Examiner* — Raul J Rios Russo
(74) *Attorney, Agent, or Firm* — Snell & Wilmer L.L.P.

(57) ABSTRACT

A system for evaluation of soiling of solar photovoltaic (PV) modules may comprise a first pair of solar PV modules exposed to the elements, a second pair of solar PV modules enclosed within a protective housing having a glass cover; a component coupling the glass cover to the protective housing. The component may be configured to displace the glass cover for a limited period of time to temporarily expose the second pair of solar PV modules to the atmospheric elements.

10 Claims, 3 Drawing Sheets

(51) Int. Cl.

| | |
|---|---|
| *H02S 40/10* | (2014.01) |
| *H02S 30/10* | (2014.01) |
| *H02S 50/00* | (2014.01) |
| *H01L 31/042* | (2014.01) |
| *H02J 7/00* | (2006.01) |
| *G01N 27/414* | (2006.01) |
| *G01N 33/00* | (2006.01) |
| *G01R 31/00* | (2006.01) |
| *H01L 21/66* | (2006.01) |

(52) U.S. Cl.
CPC ......... *G01N 27/4148* (2013.01); *G01N 33/00* (2013.01); *H01L 31/042* (2013.01); *H02J 7/00* (2013.01); *H02S 30/10* (2014.12); *H02S 40/10* (2014.12); *H02S 50/00* (2013.01); *G01R 31/003* (2013.01); *H01L 22/34* (2013.01); *H01L 2924/00* (2013.01); *H01L 2924/0002* (2013.01); *H01L 2924/00014* (2013.01)

(58) Field of Classification Search
CPC ... G01N 27/4145; G01N 27/414; G01N 33/00
USPC .................................... 324/61, 65, 71.1, 71.5
See application file for complete search history.

(56) References Cited

U.S. PATENT DOCUMENTS

| | | | | |
|---|---|---|---|---|
| 2013/0168339 | A1* | 7/2013 | Anderson | F24S 25/16 211/41.1 |
| 2015/0280644 | A1* | 10/2015 | Gostein | H02S 50/00 356/72 |
| 2017/0194897 | A1* | 7/2017 | Lopez | H02S 40/10 |
| 2017/0338771 | A1* | 11/2017 | Gostein | H02S 50/15 |
| 2018/0254741 | A1* | 9/2018 | Jones | B08B 1/008 |
| 2018/0278202 | A1* | 9/2018 | Gostein | H02S 40/10 |

OTHER PUBLICATIONS

J. Cano, J.J. John, S. Tatapudi, and G. TamizhMani, "Effect of Tilt Angle on Soiling of Photovoltaic Modules," IEEE Photovoltaic Specialist Conference (PVSC), 2014.

J. John, V. Rajasekar, S. Bopanna, S. Tatapudi, G. TamizhiMani, "Influence of soiling layer on QE, Spectral Reflectance on c-Si PV Modules" IEEE PVSC 2014.

J. John, V. Rajasekar, S. Bopanna, S. Tatapudi and G. TamizMani, "Angle of Incidence Effects on Soiled PV modules", SPIE 2014.

J. John, V. Rajasekar, S. Chattapadhyay, A. Kottantharayil, G. TamizhMani, "Quantification and Modeling of Spectral and Angular Losses of Naturally Soiled PV Modules," IEEE Journal of Photovoltaics, vol. 5, Nov. 2015.

J. Mallineni, K. Yedidi, S. Shrestha, B. Knisely, S. Tatapudi, J. Kuiche and G. TamizhiMani, "Soiling Losses of Utility-Scale PV Systems in Hot-Dry Desert Climates: Results from Four 4-16 Years Old Power Plants," IEEE Photovoltaic Specialists Conference, 2014.

S. Boppana, V. Rajasekar and G. TamizhMani, Working towards the Development of a Standardized Artificial Soiling Method, IEEE Photovoltaic Specialists Conference, 2015.

V. Rajasekar, S. Boppana, G. TamizhMan, "Angle of Incidence Effect on Five Soiled Modules from Five Different PV Technologies" IEEE Photovoltaic Specialists Conference, 2015.

B. King, G. TamizhMani, S. Tatapudi, V. Rajasekar and S. Boppanna, "Regional Soiling for PV: Design, Calibration and Installation" IEEE Photovoltaic Specialists Conference, 2015.

G. TamizhMani, B. King, A. Venkatesan, C. Deline, A. Pavgi, S. Tatapudi, J. Kuitche, A. Chokor and M. El Asmar, "Regional Soiling Stations for PV: Soiling Loss Analysis," IEEE Photovoltaic Specialists Conference, 2016.

S. Boppana, "Outdoor Soiling Loss Characterization Statistical Risk Analysis of Photovoltaic Power Plants," (free downloading at: https://respository.asu.edu/attachments/150806/content/Boppana_asu_0010N_15080.pdf).

M. Naeem and G. TamizhMani, "Cleaning frequency optimization for soiled photovoltaic modules," IEEE Photovoltaic Specialists Conference, 2015.

M. Naeem, "Soiling of Photovoltaic Modules: Modeling and Validation of Location-Specific Cleaning Frequency Optimization," MS Thesis, Arizona State University, 2014 (free downloading at: https://respository.asu.edu/attachments/140875/content/Naeem_asu_0010N_14391.pdf).

V. Rajasekhar "Indoor Soiling Method and Outdoor Statistical Risk Analysis of Photovoltaic Power Plants", MS Thesis, Arizona State University, 2015 (free downloading at: https://resository.asu.edu/attchments/150884/content/Rajasekar_asu_0010N_14973.pdf).

* cited by examiner

SOLAR PHOTOVOLTAIC WATERLESS SOILING MONITORING SYSTEMS AND METHODS

CROSS-REFERENCE TO RELATED APPLICATIONS

This application claims priority to, and the benefit of, U.S. Provisional Patent Application No. 62/507,968 filed on May 18, 2017 and entitled "SOLAR PHOTOVOLTAIC WATERLESS SOILING MONITORING SYSTEMS AND METHODS." The entire contents of the foregoing application are hereby incorporated by reference for all purposes.

FEDERALLY SPONSORED RESEARCH OR DEVELOPMENT

This invention was made with government support under grant number UGA-0-41025-48 awarded by the Department of Energy/National Renewable Energy Laboratory. The Government has certain rights in the invention.

TECHNICAL FIELD

The present disclosure relates to renewable energy such as solar power, and in particular to monitoring and characterization of soiling losses associated with solar photovoltaic modules, panels, or plants.

BACKGROUND

Soiling on the glass superstrates of solar photovoltaic (PV) modules reduces the amount of sunlight reaching the solar cells and decreases both current and power of the power plant. Soiling is a major issue in many climatic regions, especially in the desert climatic region due to infrequent rain falls. Accordingly, improved systems and methods for evaluating soiling losses associated with solar PV modules remain desirable.

SUMMARY

In various exemplary embodiments, a system for evaluation of soiling of solar photovoltaic (PV) modules may comprise a first pair of solar PV modules exposed to the elements, a second pair of solar PV modules enclosed within a protective housing having a glass cover, and a component coupling the glass cover to the protective housing, the component configured to displace the glass cover for a limited period of time to temporarily expose the second pair of solar PV modules to atmospheric elements.

In an exemplary embodiment, the first pair of solar PV modules comprises a first soiled module and a second soiled module, and the second pair of solar PV modules comprises a first clean module and a second clean module. The system may further comprise a wireless communication device in electronic communication with the first pair of solar PV modules and the second pair of solar PV modules, the wireless communication device operable to transmit data obtained from the first pair of solar PV modules and the second pair of solar PV modules to a remote location. The system may be operable to provide information regarding soiling of the PV modules without the system being coupled to a water supply or an electric grid connection. The first pair of solar PV modules and second pair of solar PV modules may be coupled to an aluminum sheet configured to reflect sunlight and reduce solar heat gain. The aluminum sheets may be coupled to a base plate comprising an opening configured to reduce a wind load on the system. The system may further comprise a battery electrically coupled to and configured to provide power to the wireless communication device. The system may further comprise a PV panel electrically coupled to and configured to recharge the battery. Each solar PV module of the first pair of solar PV modules and second pair of solar PV modules may comprise two halves of a monocrystalline silicon cell. The base plate may be mounted to an anodized aluminum frame structure. The component may be a rod configured to allow rotational movement of the glass cover. The anodized aluminum frame structure may be a tripod configured to distribute weight of the system on a ground surface.

In another exemplary embodiment, a method for determining a status of a solar photovoltaic (PV) system may comprise providing a first pair of PV modules exposed to the elements, providing a second pair of PV modules covered by a shutter, opening the shutter of the second pair of PV modules for a period of time, measuring a first voltage of a first module of the first pair of PV modules, measuring a second voltage of a first module of the second pair of PV modules, and calculating a first ratio between the first voltage and the second voltage to determine a soiling loss factor (SLF).

In various exemplary embodiments, the method may further comprise measuring a third voltage of a second module of the first pair of PV modules and a fourth voltage of a second module of the second pair of PV modules and calculating a second ratio between the third voltage and the fourth voltage to provide a first redundant SLF measurement. The method may further comprise calculating a third ratio between the first voltage and the fourth voltage to provide a second redundant SLF measurement. The method may further comprise calculating a fourth ratio between the third voltage and the second voltage to provide a third redundant SLF measurement. The method may further comprise measuring a fifth voltage of the first module of the second pair of PV modules and a sixth voltage of the second module of the second pair of PV modules while the shutter is closed. The method may further comprise calculating a fifth ratio between the fifth voltage and the second voltage to determine a soiled glass cover transmittance (SGT). The method may further comprise calculating a sixth ratio between the sixth voltage and the second voltage to provide a first redundant SGT measurement. The method may further comprise calculating a seventh ratio between the first voltage and the fifth voltage to determine a clean glass cover transmittance (CGT).

The foregoing features and elements may be combined in various combinations without exclusivity, unless expressly indicated otherwise. These features and elements as well as the operation thereof will become more apparent in light of the following description and the accompanying drawings. It should be understood, however, the following description and drawings are intended to be exemplary in nature and non-limiting. The contents of this section are intended as a simplified introduction to the disclosure, and are not intended to limit the scope of any claim.

BRIEF DESCRIPTION OF THE DRAWINGS

With reference to the following description and accompanying drawings.

DETAILED DESCRIPTION

Figure 1:
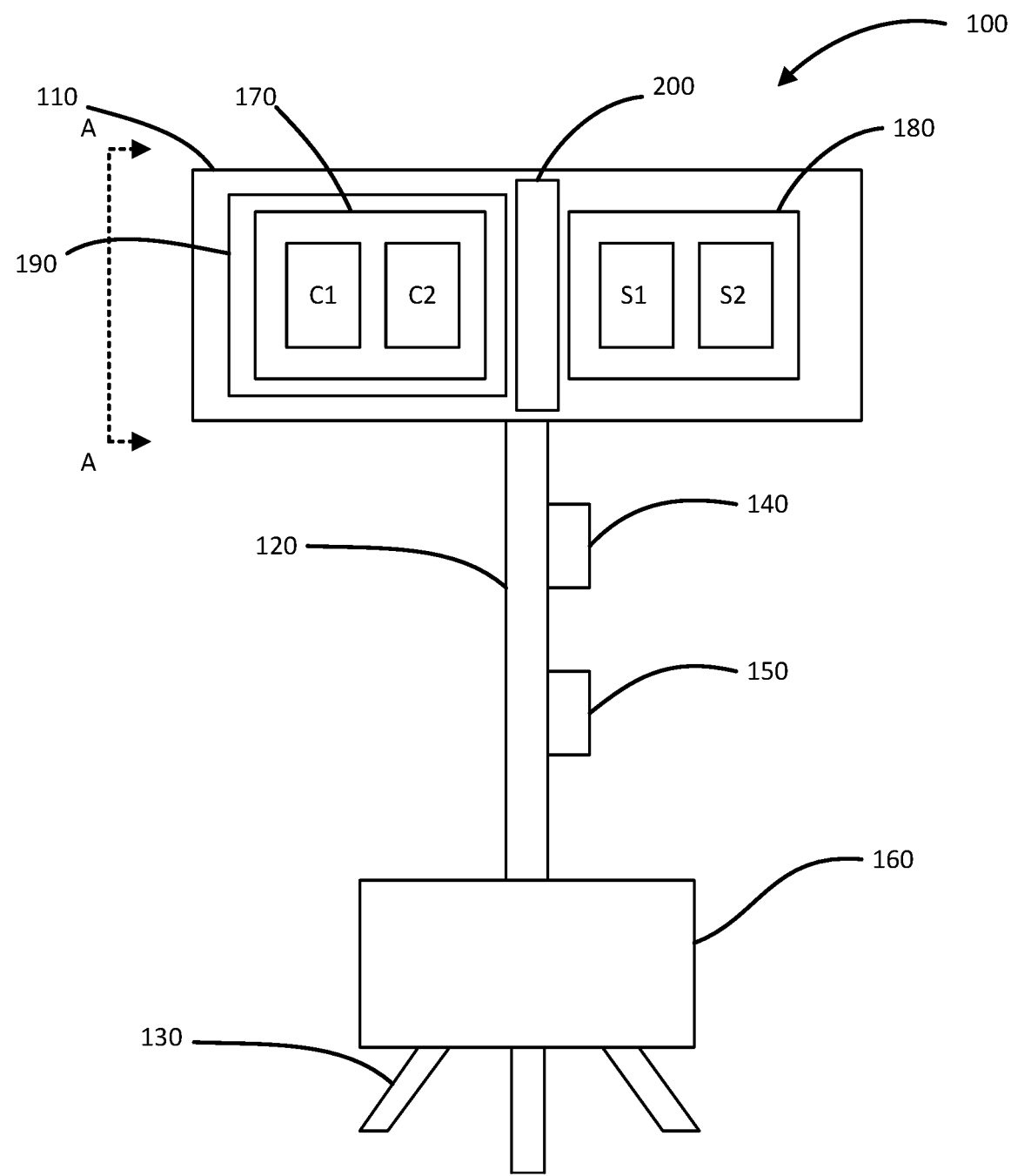
FIG. 1 illustrates an exemplary soiling evaluation system in accordance with an exemplary embodiment.

The following description is of various exemplary embodiments only, and is not intended to limit the scope, applicability or configuration of the present disclosure in any way. Rather, the following description is intended to provide a convenient illustration for implementing various embodiments including the best mode. As will become apparent, various changes may be made in the function and arrangement of the elements described in these embodiments without departing from principles of the present disclosure.

For the sake of brevity, conventional techniques for photovoltaic cell characterization, construction, and use, as well as conventional approaches for soiling monitoring and remediation, and/or the like may not be described in detail herein. Furthermore, the connecting lines shown in various figures contained herein are intended to represent exemplary functional relationships and/or physical couplings between various elements. It should be noted that many alternative or additional functional relationships or physical connections may be present in a practical solar photovoltaic soiling monitoring system.

It will be appreciated that, while exemplary embodiments disclosed herein are directed to solar photovoltaic systems, principles of the present disclosure may be applied to various other technologies wherein soiling associated with a surface exposed to the elements may be desired to be characterized.

Soiling on the glass superstrates of photovoltaic (PV) modules reduces the amount of sunlight reaching the solar cells and decreases both current and power of the power plant. Soiling is considered as a major operations and maintenance (O&M) expense by the power plant owners, and conventional energy estimation models typically assume a 3% annual de-rating factor for the soiling losses. However, the soiling loss could heavily be influenced by the tilt angle (horizontal tilt, latitude tilt, etc.), site condition or surrounding (urban, rural, agricultural, etc.), installation type (fixed ground mount, fixed rooftop mount, 1-axis tracking, etc.) and the season (dry, windy, humid or rainy). The data obtained from the soiling stations can be used to determine the location- and tilt-specific soiling loss and as a tool to determine the cleaning frequency and if module cleaning is an economically viable option for the specific PV plant. An accurate soiling loss determination is especially desirable for desert climatic locations as they typically experience heavy soiling losses during the periods of higher energy demand with higher energy costs.

Principles of the present disclosure may be utilized to provide PV plant operators, PV O&M service companies and others with a soiling monitoring station, for example a system suitable to determine the location- and tilt-specific soiling loss at a site and serve as a tool to determine if module cleaning is an economically viable option for the specific PV plant. As compared to prior approaches, for example water-based soiling monitoring approaches, exemplary systems disclosed herein do not require a water supply. Other existing/commercial solutions for soiling loss measurements include soiling stations that require water-based cleaning of a single reference sensor without any data redundancy and such systems offer only one soiling loss factor/ratio. An exemplary waterless web-monitored soiling station (as disclosed herein) provides a fully autonomous approach to measure and record at least thirteen different sensor ratios to determine location and tilt-specific soiling loss factors with redundancy for a greater level of confidence on the collected data. In addition, an exemplary system does not require any connections to water and/or electricity.

In accordance with various exemplary embodiments, and with reference now to FIG. 1, to determine cleaning frequency and to quantify the site-specific soiling rate (e.g., g/m2/day) and daily annual soiling loss (%) over long term in the field, an exemplary soiling monitoring system 100 may be provided. Soiling monitoring system may comprise a base panel 110 configured to be mounted to a body 120 such that base panel may be elevated above the surrounding areas, thereby allowing panel to receive direct sunlight. Body 120 may comprise a stiff structural element, for example an anodized aluminum frame structure to provide adequate support for base panel 110, while still allowing relatively easy maneuvering and transport of soiling monitoring system 100. The aluminum frame structure may be installed on a base 130 comprising a tripod stand which can easily be mounted on the ground within a limited amount of time (the aluminum frame structural design is flexible enough to be mounted on rooftop structures or 1-axis tracker platforms/arrays depending on the power plant tracking mechanism). Base 130 may be configured to evenly distribute weight of soiling monitoring system 100 on the ground. While in FIG. 1 base 130 is depicted as a tripod, base 130 is not limited in this regard and may comprise any suitable structure capable of distributing weight of soiling monitoring system 100.

In exemplary embodiments, base panel 110 may comprise a first station 170 and a second station 180. To avoid monitoring of temperatures of the sensor/solar cells (for temperature correction of monitored current), the first station 170 and the second station 180 may be mounted on two large thick aluminum sheets as heat spreaders/sinks with white reflecting surface to reduce the solar heat gain. A large opening 200 may be situated between first station 170 and second station 180 to reduce a wind load on soiling monitoring system 100. Each station may contain two PV modules (and/or other sensors) and each module may contain two half-cells (for example, cut from a single monocrystalline silicon cell). Other numbers of cells may be utilized, as desired. The PV modules may be installed co-planar to each other with the PV modules of first station 170 being designed to be "clean" (as indicated by C1 and C2) and the PV modules of second station 180 being designed to be "soiled" (as indicated by S1 and S2). PV modules S1 and S2 of second station 180 may be configured to act as a reference for PV modules C1 and C2 of first station 170, and/or vice versa.

With continued reference to FIG. 1, soiling monitoring system 100 may comprise a data acquisition system 140 (or "DAS") configured to receive and process data collected from PV modules C1, C2, S1, and S2. DAS 140 may be electrically coupled to a battery 150 configured to power DAS 140. Battery 150 may comprise a secondary cell or accumulator battery, such as for example, a lithium-ion, nickel-metal hydride, nickel-cadmium, lead-acid, or other suitable type of battery. Battery 150 may be electrically coupled to PV panel 160 such that PV panel 160 may charge battery 150. In this way, soiling monitoring system 100 may act as a self-sustaining system not dependent on outside energy sources.

DAS 140 may comprise a data logger that is installed to collect the data throughout the year (or it can be programmed to be operated during the soiling seasons only). The data logger can collect the data at any time interval specified by the user. A recommended data logging for fixed tilt PV arrays is: every hour and on the hour between 1 pm of previous day and 11 am of the following day; every minute or every second (depending on the data logger and data provider contract—cellular etc.) between 11 am and 1 pm (an important period) every day. The data logger transmits the data wirelessly which can easily be monitored and downloaded for analysis. A recommended data logging for 1-axis tracking PV arrays is: every hour and on the hour between 11 am of previous day and 9 am of the following day; every minute or every second between 9 am and 11 am (an important period) every day. The fault conditions, if any, may be communicated to stakeholders by emails or other suitable communications mechanism if needed.

Figure 2:
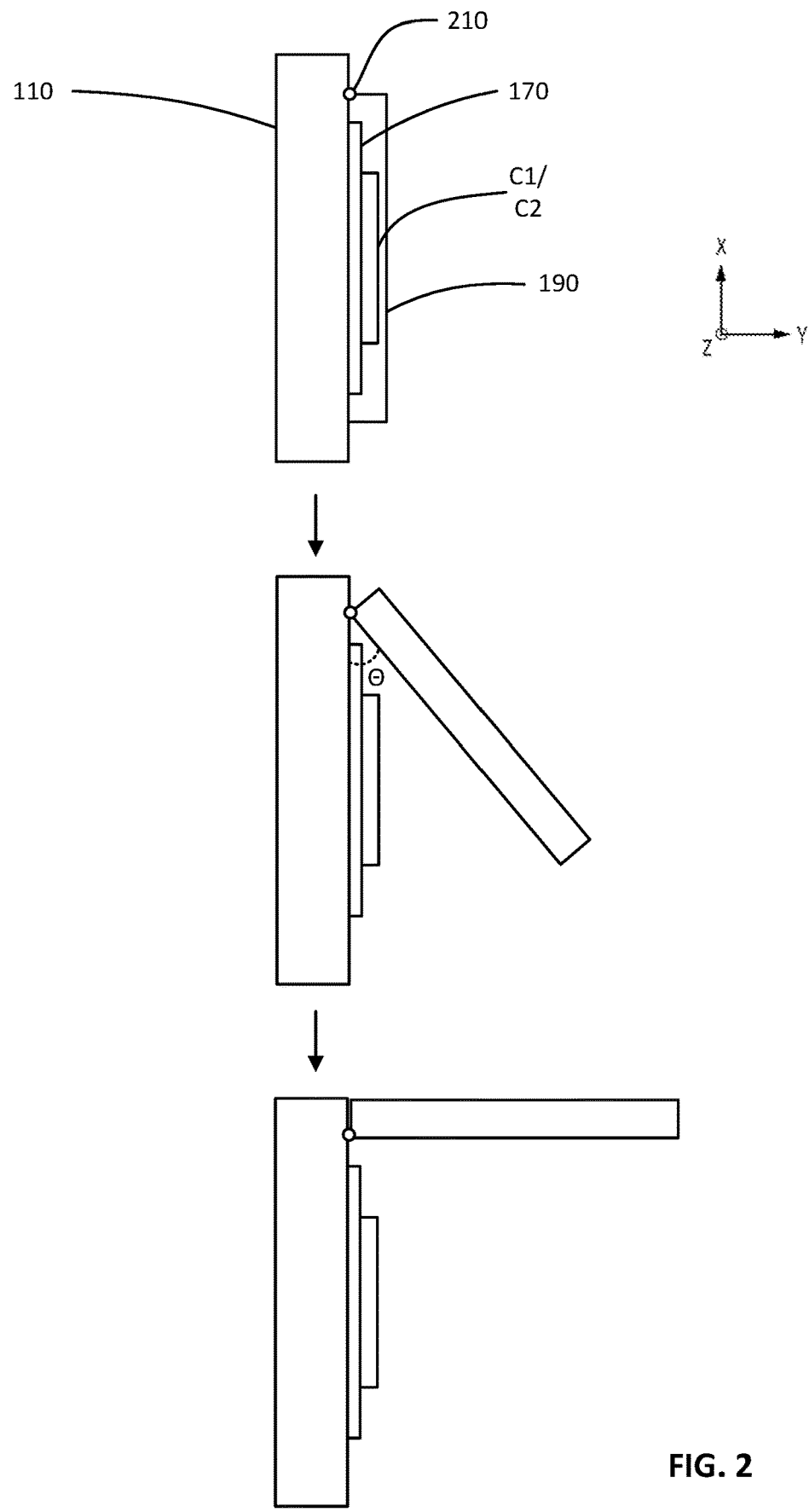
FIG. 2 illustrates operation of a "clean" PV module portion of a soiling evaluation system in accordance with an exemplary embodiment.

In an exemplary embodiment, and with reference now to FIG. 2, first station 170 is depicted from a side view as shown by line A-A in FIG. 1. Clean PV modules C1 and C2 of first station 170 may be covered with a shutter 190 comprising, for example a sheet of glass comprising approximately 94% transmittance. Other covers comprising alternative materials and/or transmittances may be desired. During the critical period every day, shutter 190 may be rotated about rod 210 (about the z-axis) to form an angle, Θ with base panel 110 and lifted away from the clean PV modules' plane for a pre-determined period (few seconds to few minutes) using an actuator. The shutter 190 may be made of a transparent material other than glass; moreover, the cover may be slid, pivoted, or otherwise removed from covering the clean PV modules C1, C2 via any suitable mechanism or components, for example springs, actuators, and/or the like.

Figure 3:
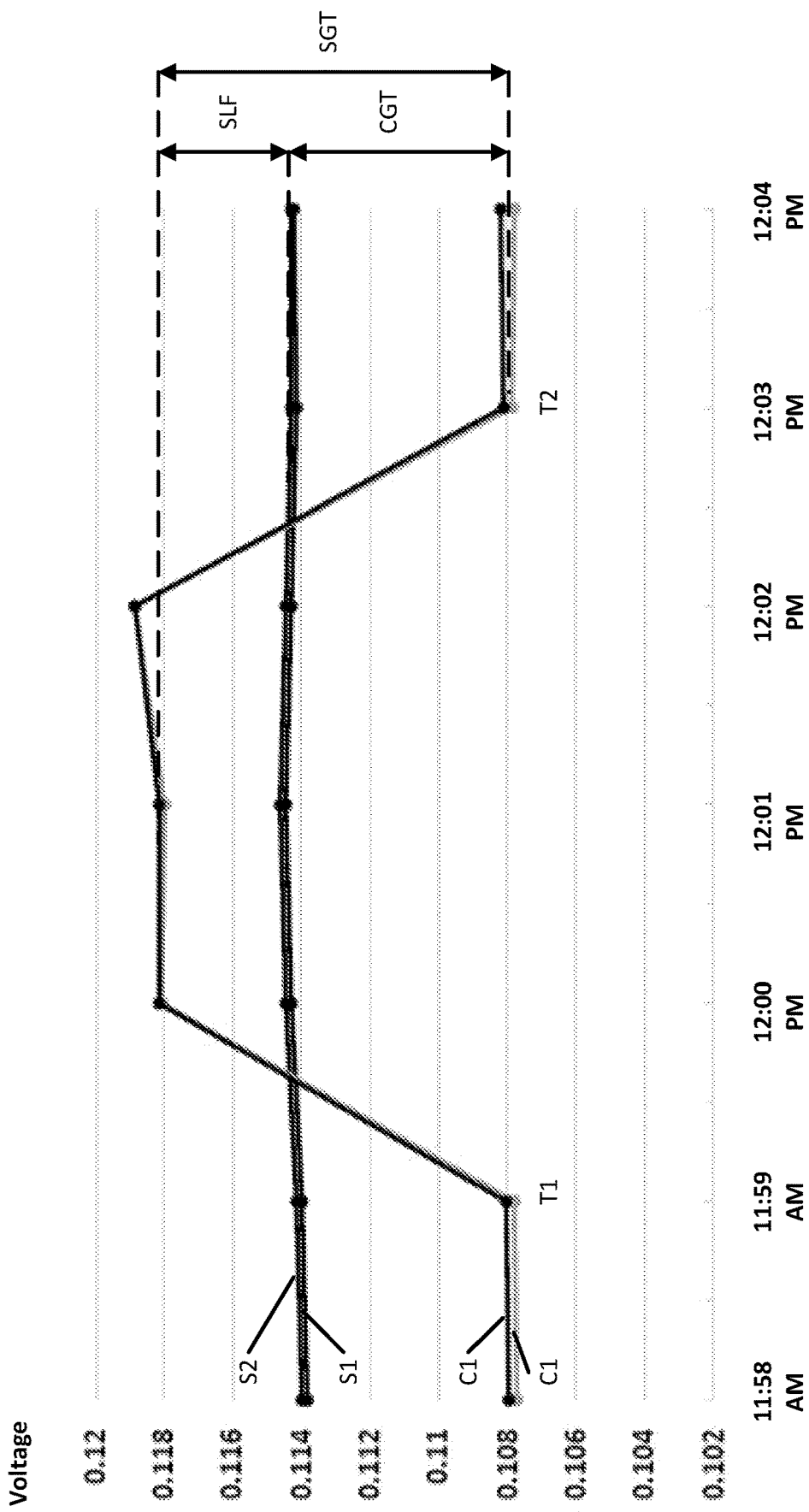
FIG. 3 illustrates a graphical representation of data obtained from operation of an exemplary soiling evaluation system in accordance with an exemplary embodiment.

With reference to FIG. 3, soiling monitoring system 100 may be used to determine cleaning frequency and to quantify the site-specific soiling rate (i.e., in g/m2/day) and daily/annual soiling loss (%) over long term in the field. In an exemplary soiling monitoring system 100 the current output of a soiled PV module may be compared with that of a coplanar installed clean sensor. The soiling loss factor (or "SLF") is a ratio between the current outputs of soiled and cleaned modules. The integrated area of the downward peaks of the SLF time series plots for a year provides the annual soiling loss for the system.

For example, moving from left to right, a voltage of clean PV modules C1 and C2 of first station 170 and soiled PV modules S1 and S2 of second station 180 may be plotted as a function of time. Initially, shutter 190 may be closed over clean modules PV C1 and C2 of first station 170. A voltage reading of soiled PV modules S1 and S2 may be relatively higher than those of clean PV modules C1 and C2 when shutter 190 is closed due to the soiling of shutter 190. At time T1, shutter 190 may begin to open and a measured voltage associated with clean PV modules C1 and C2 may increase in a linear fashion due to the presence of light unimpeded by shutter 190. Upon reaching a fully open position, a voltage associated with clean PV modules C1 and C2 may be substantially constant. The process may then begin to reverse at T2 and shutter 190 may begin to close, thereby decreasing a measured voltage associated with clean PV modules C1 and C2, also in a linear fashion. Soiled PV modules S1 and S2 may maintain a relatively constant voltage between T1 and T2. A ratio between a measured voltage of C1 or C2 while shutter 190 is in a fully closed position over a measured voltage of C1 or C2 while shutter 190 is in a fully open position may be defined as the soiled glass cover transmittance (or "SGT"). In the case of the test results depicted in FIG. 3, the SGT may be approximately 0.108/0.118 or 0.915. A ratio between a measured voltage of C1 or C2 in a fully closed position over a measured voltage of S1 or S2 may be defined as the clean glass cover transmittance (or "CGT"). In the case of the test results depicted in FIG. 3, the CGT may be approximately 0.108/0.114 or 0.947.

The data collected during these few seconds or few minutes are utilized to determine the SLFs, soiled glass cover transmittance (SGT), clean glass cover transmittance (CGT), and cemented/loose soil ratio. Other data collected during the day and night may be used for various analysis including soiling effect on angle of incidence losses, bird dropping, cemented/loose soil ratio, effectiveness of anti-soiling coatings, detection of microorganism growth on soiled sensors, and the like. The glass shutter may be lifted away from the sensors using a small programmed actuator powered by battery 150 which is maintained at full state of charge using PV panel 160 installed on base 130.

In contrast to prior, manual one-cell based automated water-based cleaning soiling stations which offer only one ratio, an exemplary automated waterless web-monitored cleaning station uses high-quality two-cell PV modules as sensors allowing the measurement and recording of at least thirteen different sensor ratios between clean/clean, soiled/soiled and clean/soiled with and without glass cover (remarkable data redundancy for higher confidence level on the collected data; determination of ratio between cemented and loose soil).

For example, referring to Table 1 below, thirteen ratios that may be measured are listed, wherein C1 and C2 refer to clean PV modules, S1 and S2 refer to soiled PV modules, CC1 and CC2 refer to covered clean PV modules, CC1*a* and CC2*a* refer to covered clean PV modules after shutter 190 has been closed, and CC1*b* and CC2*b* refer to covered clean PV modules before shutter 190 has been opened. Ratio code 1 of C1/C2 may be used to determine malfunctioning of one of clean PV modules C1 or C2. Ratio code 2 of S1/S2 may be used to determine soiling-non uniformity between soiled PV module S1 and soiled PV module S2. Ratio codes 3-6 may be used to determine the soiling loss factor as described above and also to provide redundancy for such measurements. Ratio code 7 of CC1 and CC2 may be used to determine soiling non-uniformity between closed clean PV module CC1 and closed clean PV module CC2. Ratio codes 8-11 may be used to determine a surface anti-soiling coating effectiveness or loose soil presence and also to provide redundancy for such measurements. Ratio codes 12 and 13 may be used to determine a cemented to loose soil ratio and also to provide redundancy for such a measurement.

TABLE 1

| Ratio Code | Sensor Ratio |
| --- | --- |
| 1 | C1/C2 |
| 2 | S1/S2 |
| 3 | S1/C1 |
| 4 | S2/C1 |
| 5 | S1/C2 |
| 6 | S2/C2 |
| 7 | CC1/CC2 |
| 8 | S1/CC1 |

TABLE 1-continued

| Ratio Code | Sensor Ratio |
|---|---|
| 9 | S2/CC1 |
| 10 | S1/CC2 |
| 11 | S2/CC2 |
| 12 | CC1b/CC1a |
| 13 | CC2b/CC2a |

It will be appreciated that, while various exemplary embodiments are discussed in connection with a solar module, module, or the like, principles of the present disclosure may desirably be utilized in connection with characterization of any suitable sensor, for example an optical sensor, an infrared sensor, an ultraviolet sensor, a radiometer, and/or the like.

While the principles of this disclosure have been shown in various embodiments, many modifications of structure, arrangements, proportions, the elements, materials and components, used in practice, which are particularly adapted for a specific environment and operating requirements may be used without departing from the principles and scope of this disclosure. These and other changes or modifications are intended to be included within the scope of the present disclosure.

The present disclosure has been described with reference to various embodiments. However, one of ordinary skill in the art appreciates that various modifications and changes can be made without departing from the scope of the present disclosure. Accordingly, the specification is to be regarded in an illustrative rather than a restrictive sense, and all such modifications are intended to be included within the scope of the present disclosure. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, required, or essential feature or element.

As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. Also, as used herein, the terms "coupled," "coupling," or any other variation thereof, are intended to cover a physical connection, an electrical connection, a magnetic connection, an optical connection, a communicative connection, a functional connection, and/or any other connection. When language similar to "at least one of A, B, or C" or "at least one of A, B, and C" is used in the specification or claims, the phrase is intended to mean any of the following: (1) at least one of A; (2) at least one of B; (3) at least one of C; (4) at least one of A and at least one of B; (5) at least one of B and at least one of C; (6) at least one of A and at least one of C; or (7) at least one of A, at least one of B, and at least one of C.

What is claimed is:

1. A method for determining a soiling status of a solar photovoltaic (PV) system, the method comprising:

providing, at a location near the solar PV system, a first pair of PV modules exposed to the elements;

providing, at the location, a second pair of PV modules covered by a shutter;

opening the shutter of the second pair of PV modules for a period of time;

measuring a first voltage of a first module of the first pair of PV modules;

measuring a second voltage of a first module of the second pair of PV modules;

calculating a first ratio between the first voltage and the second voltage to determine a soiling loss factor (SLF);

measuring a third voltage of a second module of the first pair of PV modules and a fourth voltage of a second module of the second pair of PV modules and calculating a second ratio between the third voltage and the fourth voltage to provide a first redundant SLF measurement;

calculating a third ratio between the first voltage and the fourth voltage to provide a second redundant SLF measurement;

calculating a fourth ratio between the third voltage and the second voltage to provide a third redundant SLF measurement; and measuring a fifth voltage of the first module of the second pair of PV modules and a sixth voltage of the second module of the second pair of PV modules while the shutter is closed.

2. The method of claim 1, further comprising calculating a fifth ratio between the fifth voltage and the second voltage to determine a soiled glass cover transmittance (SGT).

3. The method of 1, further comprising calculating a seventh ratio between the first voltage and the fifth voltage to determine a clean glass cover transmittance (CGT).

4. The method of claim 1, further comprising cleaning, responsive to a comparison between the soiling loss factor and a soiling threshold, the solar PV system to reduce soiling.

5. The method of claim 1, wherein a wireless communication device is in electronic communication with the first pair of solar PV modules and the second pair of solar PV modules, the wireless communication device operable to transmit data obtained from the first pair of solar PV modules and the second pair of solar PV modules to a remote location.

6. The method of claim 1, wherein the first pair of solar PV modules and second pair of solar PV modules are each coupled to an aluminum sheet configured to reflect sunlight and reduce solar heat gain.

7. The method of claim 6, wherein the aluminum sheets are coupled to a base plate comprising an opening configured to reduce a wind load on the system.

8. The method of claim 7, wherein the base plate is mounted to an anodized aluminum frame structure.

9. The method of claim 8, wherein the anodized aluminum frame structure is a tripod configured to distribute weight on a ground surface.

10. The method of claim 1, wherein each solar PV module of the first pair of solar PV modules and second pair of solar PV modules comprises two halves of a monocrystalline silicon cell.

* * * * *